(12) United States Patent
Sugawara

(10) Patent No.: US 9,439,839 B2
(45) Date of Patent: Sep. 13, 2016

(54) COSMETIC SOLUTION, METHOD FOR PRODUCING COSMETIC SOLUTION, AND COSMETIC METHOD

(76) Inventor: Yukako Sugawara, Ichinoseki (JP)

(*) Notice: Subject to any disclaimer, the term of this patent is extended or adjusted under 35 U.S.C. 154(b) by 0 days.

(21) Appl. No.: 14/116,594

(22) PCT Filed: Apr. 17, 2012

(86) PCT No.: PCT/JP2012/002633
§ 371 (c)(1),
(2), (4) Date: Nov. 19, 2013

(87) PCT Pub. No.: WO2012/153466
PCT Pub. Date: Nov. 15, 2012

(65) Prior Publication Data
US 2014/0088040 A1    Mar. 27, 2014

(30) Foreign Application Priority Data

May 10, 2011 (JP) ................. 2011-105123
Oct. 17, 2011 (JP) ................. 2011-228093

(51) Int. Cl.
| | | |
|---|---|---|
| A61K 8/02 | (2006.01) | |
| A61K 8/73 | (2006.01) | |
| A61Q 19/00 | (2006.01) | |
| A61K 8/34 | (2006.01) | |
| A61K 8/365 | (2006.01) | |

(52) U.S. Cl.
CPC ............. *A61K 8/0204* (2013.01); *A61K 8/345* (2013.01); *A61K 8/365* (2013.01); *A61K 8/735* (2013.01); *A61Q 19/00* (2013.01); *A61Q 19/007* (2013.01); *A61K 2800/31* (2013.01)

(58) Field of Classification Search
CPC ...... A61Q 19/00; A61K 8/345; A61K 8/735; A61K 8/0204; A61K 200/31
USPC ........................................... 514/54
See application file for complete search history.

(56) References Cited

U.S. PATENT DOCUMENTS

| | | | | |
|---|---|---|---|---|
| 3,248,333 A | * | 4/1966 | O'Roark ................ | C11D 1/12 510/151 |
| 5,733,562 A | | 3/1998 | Lee | |
| 5,942,498 A | * | 8/1999 | Falk et al. ................ | 514/54 |
| 5,968,528 A | * | 10/1999 | Deckner et al. ............ | 424/401 |
| 6,491,933 B2 | * | 12/2002 | Lorenzi ................ | A61Q 19/10 424/401 |

FOREIGN PATENT DOCUMENTS

| | | |
|---|---|---|
| JP | 2006-182750 A | 7/2006 |
| KR | 10-2010-0120743 A | 11/2010 |
| WO | 2011/070620 A1 | 6/2011 |

OTHER PUBLICATIONS

Penniston et al, J. Endourol, 2008, 22(3), 567-70.*
Soap & Detergent Association, 1990, pp. 1-27.*
Kakoki et al, Fragrance Journal, 2005, 33(10), 14-19, English Translation.*
Sekine, Shin Keshohin Handbook, 2006, Oct. 30, 508-509, English Translation.*
Gova Ingredients, Gova; 2006, pp. 1-3.*
Organic Glow, 2009, pp. 1-3.*
Japan Patent Office, "Written Opinion of the International Searching Authority for PCT/JP2012/002633," Nov. 12, 2013.
Japan Patent Office, "International Search Report for PCT/JP2012/002633," Jul. 17, 2012.
Shigeru Sekine, "Shin Keshohin Handbook," Nikko Chemicals Co., Ltd., Oct. 30, 2006, p. 508-509.
Hiroyuki Kakoki, "Saikin no Hoshitsu Kenkyu to Hoshitsuzai no Kaihatsu Doko- Hoshitsuzai Kaihatsu no Rekishi o Fumaete-," Fragrance Journal, Oct. 15, 2005, vol. 33, No. 10, p. 14-19.
Singapore Patent Office, "Office Action for Singapore Patent Application No. 2013082896," Jan. 26, 2016.

* cited by examiner

*Primary Examiner* — Ganapathy Krishnan
(74) *Attorney, Agent, or Firm* — Manabu Kanesaka

(57) ABSTRACT

Provided are a cosmetic solution and a method for producing the cosmetic solution, the cosmetic solution being easy to store and also easy to handle during use, and moreover having a high moisturizing function, without the use of a preservative. Hyaluronic acid/or a hyaluronic acid compound is dispersed in a polyvalent alcohol, also, an organic acid and/or organic acid salt different from the hyaluronic acid and/or hyaluronic acid compound is dispersed in a polyvalent alcohol such that it contains no water. The solution contains 0.01 to 2.0 wt % hyaluronic acid and/or hyaluronic acid compound 97 wt % or more polyvalent alcohol, is weakly acidic; i.e. 5≤pH<7 due to the organic acid and/or organic acid salt.

11 Claims, 3 Drawing Sheets

FIG. 3

| Component | Examples | | | | | | | Comparative Examples |
| --- | --- | --- | --- | --- | --- | --- | --- | --- |
| | 1 | 2 | 3 | 4<br>Glycerin:BG | 5<br>Glycerin:BG | 6 | 7 | 1 |
| Hyaluronic acid Na (60) | 0.5 | 1.0 | 2.0 | 0.5 | 0.5 | 0.5 | 0.5 | |
| Citric acid | 0.030 | 0.030 | 0.030 | 0.030 | 0.030 | 0.030 | 0.030 | |
| Glycerin | 99.470 | 98.970 | 97.970 | 49.735 | 9.947 | – | – | 100 |
| 1,3 butylene glycol (BG) | – | – | – | 49.735 | 89.523 | 99.470 | – | |
| Propylene glycol | – | – | – | – | – | – | 99.470 | |
| Stability | ◎ | ◎<br>(However, very viscous) | △ | ◎ | ◎ | ◎ | ◎ | ◎ |

FIG. 4

Microbial test

| | One-day cultivation | Four-day cultivation | Seven-day cultivation |
| --- | --- | --- | --- |
| Com. Ex. 2 | ×<br>(One) | ×<br>(500 or more) | ×<br>(500 or more) |
| Com. Ex. 3 | Zero | Zero | Zero |
| Example 1 | Zero | Zero | Zero |

COSMETIC SOLUTION, METHOD FOR PRODUCING COSMETIC SOLUTION, AND COSMETIC METHOD

RELATED APPLICATIONS

The present application is National Phase of International Application No. PCT/JP2012/002633 filed Apr. 17, 2012, and claims priority from Japanese Applications No. 2011-105123, filed May 10, 2011 and No. 2011-228093, filed Oct. 17, 2011.

TECHNICAL FIELD

The present invention relates to a cosmetic solution containing hyaluronic acid and/or a hyaluronic acid compound. In particular, the present invention relates to a cosmetic solution which is excellent in moisturizing power to skin and has effects of beautifying the skin by providing the skin with elasticity, moisture or firmness. The present invention also relates to the method for producing this cosmetic solution and a cosmetic method using this cosmetic solution.

BACKGROUND ART

It is generally known that hyaluronic acid and/or a hyaluronic acid compound are excellent in moisturizing power to skin and has effects of beautifying the skin by providing the skin with elasticity, moisture or firmness. Various cosmetic solutions have developed using hyaluronic acid and/a hyaluronic acid compound.

Conventionally, as a cosmetic solution containing hyaluronic acid and/or a hyaluronic acid compound, one obtained by using a sodium hyaluronate as a hyaluronic acid compound, mixing about 0.1% of the sodium hyaluronate with water, and further mixing a preservative such as phenoxy ethanol or paraben has been widely used.

In this cosmetic solution, since a preservative is contained, it irritates the skin. Therefore, this solution has defects that when it is in contact with the skin for a long period of time, it may induce systematic toxicity by percutaneous absorption, or the like.

In order to solve the problem, a technology disclosed in JP-A-2006-182750 (Patent Document 1) has conventionally been known. This is a product obtained by freeze-drying an aqueous solution comprising sodium hyaluronate, an ascorbic acid derivative and collagen. The freeze-dried powder is put in a container, and after substituting the inside of the container with a nitrogen gas, the container is sealed by a rubber stopper to eliminate the presence of oxygen, whereby the powder is preserved such that no water content is absorbed. When used, this freeze-dried powder is re-dissolved in water or in a cosmetic solution.

RELATED ART DOCUMENTS

Patent Documents

Patent Document 1: JP-A-2006-182750

SUMMARY OF THE PRESENT INVENTION

Subject to be Solved by the Present Invention

In the conventional freeze-dried product containing sodium hyaluronate, a long-term storage becomes possible by substituting the inside of the container accommodating the freeze-dried cosmetic product with a nitrogen gas, and then sealing the container with a rubber stopper. Therefore, if the container is open, long-term storage becomes impossible due to the absorption of moisture. In addition, it has a disadvantage that the powder has to be dissolved in water every time a user uses it, thereby making the handling troublesome. Further, although the powder is dissolved in water whenever it is used, the necessary amount for each use to be dissolved in water is very small. Therefore, in order to avoid such troublesome dissolution, generally, a week's supply of powder, for example, is dissolved in water to obtain an aqueous solution, and the solution is stored in a refrigerator or the like after putting in a container before use. However, by such a method, the cosmetic solution is stored for a certain period of time in the state of an aqueous solution. Therefore, there is a problem that, even though the storage time is short, the cosmetic solution may corrupt due to proliferation of microorganisms.

The present invention has been made based on the above-mentioned problem, and an object of the present invention is to provide a cosmetic solution capable of being stored easily without using a preservative, being easy to handle during use and having a high moisturizing power, a method for producing this cosmetic solution and a cosmetic method using this cosmetic solution.

Means for Solving the Subject

In order to attain the object, the cosmetic solution of the present invention is a cosmetic solution comprising hyaluronic acid and/or a hyaluronic acid compound which is obtained by dispersing hyaluronic acid and/or a hyaluronic acid compound in a polyvalent alcohol to allow the mixture to be a solution containing no water. As the hyaluronic acid compound, a hyaluronic acid salt such as sodium hyaluronate or the like can be given. In addition, a derivative of hyaluronic acid such as acetylated hyaluronic acid can be used. Further, one obtained by introducing a protective group or the like into a carboxyl group or a hydroxyl group of hyaluronic acid can be given. In the present invention, the molecular weight of hyaluronic acid and/or a hyaluronic acid compound is not particularly restricted.

Due to such a configuration, this cosmetic product becomes in a liquid state, and can be stored easily after putting in a container. In this case, since it contains no water, moisture is hardly absorbed due to the liquid state even though it contacts air, proliferation of microorganisms such as bacillus and mold is suppressed, whereby preservation stability is significantly improved. When used, a necessary amount of the solution is discharged by means of a container in the form of a well-known manual dispenser or the like. For example, the amount every time a user uses is discharged on the palm or the like, and the cosmetic solution is used as it is, or is used after mixing with fresh water. In this case, since it is a liquid, as compared with conventional powder, handling is significantly improved when it is used as it is or used after diluting with fresh water. Further, since it contains no water, mixing of a preservative becomes unnecessary. As a result, a disadvantage that the skin is irritated by the action of a preservative can be avoided, whereby the health of the skin becomes significantly improved. In addition, when applied to the skin, hyaluornic acid and/or a hyaluronic acid compound exhibits moisturizing function by the cooperation of a polyvalent alcohol, and as a result, moisture-retaining property of the skin is enhanced, whereby the skin is imparted with elasticity, moisture or firmness, thus beautifying the skin.

According to need, the cosmetic solution comprises 0.01 to 2.0 wt % of the hyaluronic acid and/or the hyaluronic acid compound and 97 wt % or more of the polyvalent alcohol.

If the amount of the hyaluronic acid and/or the hyaluronic acid compound is 0.01 wt % or less, moisturizing effects are hardly exhibited. On the other hand, if the amount exceeds 2.0 wt %, the hyaluronic acid and/or the hyaluronic acid compound is not completely dissolved in the polyvalent alcohol and is likely to be precipitated easily, whereby the quality of the cosmetic solution may be lowered.

It is desired that the hyaluronic acid and/or the hyaluronic acid compound be contained in an amount of 0.1 to 1.0 wt %. Within this amount range, it is possible to allow the hyaluronic acid and/or the hyaluronic acid compound to be dispersed and dissolved completely. Further, even if the hyaluronic acid and/or the hyaluronic acid compound, which is expensive as a cosmetic solution, is not used in a large amount, a high degree of moisturizing effects can be obtained by the combined use of the hyaluronic acid and/or the hyaluronic acid compound with the polyvalent alcohol. Therefore, this gives a great advantage to consumers.

Further, according to need, the cosmetic solution has a configuration that an organic acid and/or an organic acid salt which is different from the hyaluronic acid and/or the hyaluronic acid compound is dispersed in the polyvalent alcohol to allow the mixture to be weakly acidic having a pH of $5 \leq pH < 7$.

In general, the surface of healthy skin is weakly acidic (pH 5.5 to 6.0). Immediately after washing with alkaline soap, the skin surface is more likely to be alkaline. If the cosmetic solution of the present invention is used in this state, since the cosmetic solution of the present invention is weakly acidic due to the dispersion of the organic acid and/or the organic acid salt, it is possible to recover the skin to the weakly acidic state. As a result, the barrier function or the physiological function of the skin can be kept in the normal state, the healthy skin can be maintained.

In this case, as the organic acid and/or the organic acid salt, it is advantageous to use citric acid as the organic acid and to use the citric acid in an amount of 0.0005 to 0.2 wt %. If the amount is less than 0.0005 wt %, the effect thereof is small, and the pH value becomes more neutral. If the amount exceeds 0.2 wt %, the acidity becomes too high.

The amount of the organic acid and/or the organic acid salt is preferably 0.001 to 0.1 wt %, more preferably 0.005 to 0.07 wt %, and further preferably 0.01 to 0.04 wt %.

Citric acid is an organic compound contained in oranges or the like, and one of hydroxy acids, which is a colorless or white solid at normal temperature. The reason for using citric acid is that it is an organism component which is used as a food additive and has a high degree of safety.

When the cosmetic solution containing citric acid in this amount range is dissolved in water, the resulting aqueous solution becomes ideal weak acidic. As mentioned above, the surface of healthy skin is kept its weak acidic state with a pH of 5.5 to 6.0. When the face is washed with alkaline soap, immediately after the washing, the surface of the face is alkaline. If the cosmetic solution of the present invention is used in this state, due to the presence of citric acid, the skin can recover the weakly acidic state immediately, whereby the barrier function or the physiological function of the skin can be normally retained to enable the healthy skin to be maintained.

According to need, the above-mentioned polyvalent alcohol is composed of glycerin alone or a mixture of glycerin and other polyvalent alcohols. The amount of glycerin is 50 wt % or more, preferably 80 wt % or more and more preferably 90 wt % or more relative to the weight of the cosmetic solution.

Glycerin is a natural skin moisturizing component generated by the decomposition of a sebum in the skin. Glycerin is the oldest moisturizing agent, and gives moisture and a moist feeling to the skin. Therefore, in cooperation with the hyaluronic acid and/or the hyaluronic acid compound, glycerin synergistically improves the moisturizing capability. As a result, it gives elasticity, moisture and firmness to the skin to beautify the skin.

In order to attain the above-mentioned object, the method for producing the cosmetic solution of the present invention comprises: a first dissolution step of adding to and dissolving in a solution of a polyvalent alcohol hyaluronic acid and/or a hyaluronic acid compound; and a second dissolution step of adding and dissolving an organic acid and/or an organic acid salt different from the hyaluronic acid and/or a hyaluronic acid compound to allow the mixture to be weakly acidic having a pH of $5 \leq pH < 7$.

As a result, the cosmetic solution as mentioned above is produced. In this case, it should be noted that the hyaluronic acid and/or the hyaluronic acid compound is a material which is hardly dissolved in a polyvalent alcohol. Also, it should be noted that, of the organic acid and/or the organic acid salt, there is an acid or an acid salt which is hardly dissolved in a polyvalent alcohol. Therefore, if they are added simultaneously, in the case where dissolution does not proceed, it is impossible to confirm visually the dissolution state, i.e. to confirm which material is not dissolved. However, according to the method of the present invention, these materials are added separately, i.e. the first dissolution step and the second dissolution step, it is possible to confirm the dissolution state, and as a result, dissolution can be attained without fail.

Further, the organic acid and/or the organic acid salt serves to adjust pH. In the case of the organic acid and/or the organic acid salt that affects the pH greatly even when used in a small amount, since the organic acid and/or the organic acid salt is added later in the second dissolution step, the amount thereof can be adjusted in accordance with the conditions in the first dissolution step such as the amount of the solution or the like. The adjustment of pH can be conducted without fail, and as a result, a high-quality cosmetic solution can be produced.

According to need, in the first dissolution step, the hyaluronic acid and/or the hyaluronic acid compound is added to a solution of a polyvalent alcohol of 30° C. to 70° C., followed by stirring, and then, the resulting solution is heated to 80° C.±5° C.

If the temperature of the polyvalent alcohol is lower than 30° C., stirring cannot be conducted easily due to the viscosity of the polyvalent alcohol. If the temperature of the polyvalent alcohol exceeds 70° C., due to the affection of vapor, the hyaluronic acid and/or the hyaluronic acid compound tends to adhere to the container (kettle). Desirably, the solution of a polyvalent alcohol is heated to 60° C.±5° C., and during or after this heating step, the hyaluronic acid and/or the hyaluronic acid compound is added. After the addition of the hyaluronic acid and/or the hyaluronic acid compound, the solution is heated to 80° C.±5° C. desirably with stirring. By this, the hyaluronic acid and/or the hyaluronic acid compound can be dissolved in the polyvalent alcohol without fail.

Further, according to need, in the second dissolution step, the solution is heated to 60° C.±5° C. The organic acid and/or the organic acid salt is added in this state, followed by stirring, and then the solution is cooled to 40° C. or less.

The organic acid and/or the organic acid salt is added not to the solution that has been heated to 80° C.±5° C. but to the solution of which the temperature is 60° C.±5° C. by cooling or the like. The reason therefor is that, if the temperature of the solution is high, pH adjustment is difficult. It is desired that the solution be added at an actual temperature at which the cosmetic solution is used. However, if the temperature is too low, the solution is hardly dissolved. By adding the organic acid and/or the organic acid salt to the solution of 60° C.±5° C., the organic acid and/or the organic acid salt can be dissolved easily, and in addition, an adequate pH adjustment can be conducted. Further, since the solution is cooled to 40° C. or less, stabilization can be promoted.

Further, according to need, after the second dissolution step, a filtration step is provided in which the solution is filtered to remove the hyaluronic acid and/or the hyaluronic acid compound which are not dissolved in the polyvalent alcohol.

By this, since the hyaluronic acid and/or the hyaluronic acid compound which are not dissolved in the polyvalent alcohol are removed, the solution becomes more homogeneous and hence, the quality thereof is improved.

Further, in the cosmetic method of the present invention which comprises a cosmetic solution application step in which a cosmetic solution is applied to the skin, in the cosmetic solution application step, the cosmetic solution is used as it is or is used after being mixed with water in an amount of 0.5 to 100 times larger than the dead weight of the cosmetic solution. If it is used as it is, the solution feels heavy due to its viscosity. Therefore, it is advisable to mix with water. When water is mixed, the water is used in an amount of 0.5 to 100 times, preferably 5 to 50 times, more preferably 10 to 20 times larger than the dead weight of the cosmetic solution. In this case, as compared with the conventional powder, since it is liquid, mixing is easy when used after diluting with fresh water, resulting in a significantly easy handling. In the state where it is applied to the skin, the hyaluronic acid and/or the hyaluronic acid compound cooperates with the polyvalent alcohol to exhibit moisturizing function, whereby moisture-retaining property is improved, and elasticity, moisture or firmness can be given to beautify the skin. In this case, since no antiseptic is mixed, there is no irritation to the skin caused by an antiseptic. Therefore, the state of the skin becomes quite healthy.

According to need, before the cosmetic solution application step, a face-washing step in which face washing is conducted by using a facial cleaning agent and soap containing no synthetic surfactant is used as the facial cleaning agent.

Generally, face-washing cream and face-washing foam are prepared by compounding fatty acid soap or other synthetic surfactants with a moisturizing agent, an oil component or the like. A synthetic surfactant serves to help mixing of materials which are not mixed with each other due to difference in surface tension, such as water and oil, and allows these materials to be merged with each other. It has been pointed out that such a synthetic surfactant, when applied to the skin, tends to induce an irritation reaction on the skin due to its relative capability of partially dissolving the sebum membrane of the surface skin, and that a synthetic surfactant is bonded to the stratum corneum protein of the surface skin, causing rough skin. In addition, if a synthetic surfactant is released to the environment, it affects adversely the ecology of water creatures.

Therefore, by using soap containing no synthetic surfactant as the facial cleansing agent, a state in which irritation is induced on the skin is prevented, whereby occurrence of rough skin can be avoided. As a result, the effects brought by the cosmetic solution applied at the cosmetic solution application step can be exhibited more surely.

Further, according to need, before the above-mentioned face washing step, a make up removing step is provided in which make up is removed by using a cleansing agent, and only an oily material containing no synthetic surfactant is used as the cleaning agent. Generally, oily make up cannot be removed only by a facial cleanser. Therefore, a washable make up remover obtained by compounding an oily component which is mixed well with make up with a synthetic surfactant is commonly used. As mentioned above, it has been pointed out that a synthetic surfactant tends to induce an irritation reaction on the skin, causing rough skin. However, as in the case of the present invention, by using a cleansing agent that does not contain a synthetic surfactant, occurrence of an irritation reaction on the skin can be prevented, whereby rough skin is avoided. As a result, the effects brought by the face washing step and the effects brought by the cosmetic solution applied in the cosmetic solution application step can be exhibited further surely.

Further, according to need, after the above-mentioned cosmetic solution application step, a finishing step is provided in which a finishing agent is applied to the skin, and as the finishing agent, only an oily material containing no synthetic surfactant is used. In general, a milky lotion and cream are obtained by emulsifying water, a moisturizing component and an oily component by a synthetic surfactant. By applying it to the skin on which the cosmetic solution has been applied, evaporation of water can be prevented by the blockage effect of the skin, whereby moisturizing of the skin is promoted. As mentioned above, it has been pointed out that a synthetic surfactant tends to induce an irritation reaction on the skin, causing rough skin. However, as in the case of the present invention, by using a finishing agent containing no synthetic surfactant,
occurrence of an irritation reaction on the skin can be prevented, whereby rough skin is avoided. As a result, the effects brought by the make up removing step, the effects brought by the cleansing step and the effects brought by the cosmetic solution applied in the cosmetic solution application step can be exhibited further surely.

Advantageous Effects of the Invention

According to the present invention, since the hyaluronic acid and/or the hyaluronic acid compound are dispersed in polyvalent alcohol such that no water is contained. Due to such a configuration, this cosmetic product becomes the liquid state, and can be stored easily after putting in a container. In this case, since it contains no water, moisture is hardly absorbed due to the liquid state even though it contacts air, proliferation of microorganisms such as bacillus and mold is suppressed, whereby storage stability is significantly improved. When used, a necessary amount of the solution is discharged by means of a container in the form of a well-known fixed quantity manual dispenser or the like. For example, the amount every time a user uses is discharged on the palm or the like, and the cosmetic solution is used as it is, or is used after mixing with fresh water. In this case, since it is a solution, as compared with conventional powder, handling is significantly improved when it is used as it is or used after diluting with fresh water. Further, since it contains no water, mixing of a preservative becomes unnecessary. As a result, a disadvantage that the skin is irritated by the action of a preservative can be avoided, whereby the health of the skin becomes significantly improved. In addition, when applied to the skin, hyaluronic acid and/or a hyaluronic acid compound exhibits moisturizing function by the cooperation with a polyvalent alcohol, and as a result, moisture-retaining property of the skin is enhanced, whereby the skin is imparted with elasticity, moisture or firmness, thus beautifying the skin.

Further, by adding an organic and/or an organic acid salt which is different from the above-mentioned hyaluronic acid and/or a hyaluronic acid compound which allows the skin to have a pH of $5 \leq pH < 7$, surface of the skin which has become alkaline can be recovered to the weakly acid state immediately, and the barrier function or the physiological function of the skin can be kept normal, whereby healthy skin can be maintained.

Further, according to the method for producing a cosmetic solution of the present invention, a cosmetic solution exhibiting the action and effects mentioned above can be produced. In this case, it should be noted that the hyaluronic acid and/or the hyaluronic acid compound is a material which is hardly dissolved in a polyvalent alcohol. Also, it should be noted that, of the organic acid and/or the organic acid salt, there is an acid or an acid salt, such as citric acid and/or a citric acid salt, which is hardly dissolved in a polyvalent alcohol. Therefore, if they are added simultaneously, in the case where dissolution does not proceed, it is impossible to confirm visually the dissolution state, i.e. to confirm which material is not dissolved. However, according to the method of the present invention, these materials are added in separately, i.e. the first dissolution step and the second dissolution step, it is possible to confirm the dissolution state, and as a result, dissolution can be attained without fail. Further, the organic acid and/or the organic acid salt serves to adjust pH. In the case of the organic acid and/or the organic acid salt that affects the pH greatly even when used in a small amount, since the organic acid and/or the organic acid salt is added later in the second dissolution step, the amount thereof can be adjusted in accordance with the conditions in the first dissolution step such as the amount of the solution or the like. The adjustment of pH can be conducted without fail, and as a result, a high-quality cosmetic solution can be produced.

Further, according to the cosmetic method of the present invention, by using no antiseptic or no synthetic surfactant, a state in which irritation is induced on the skin is prevented. As a result, the health of the skin can be significantly improved. Therefore, moisture-retaining property by the cosmetic solution of the invention can be improved, and elasticity, moisture and firmness are imparted to the skin, thus beautifying the skin.

MODE FOR CARRYING OUT THE INVENTION

Hereinbelow, the cosmetic solution and the method for producing the cosmetic solution of the embodiment of the present invention will be explained in detail.

Figure 1:
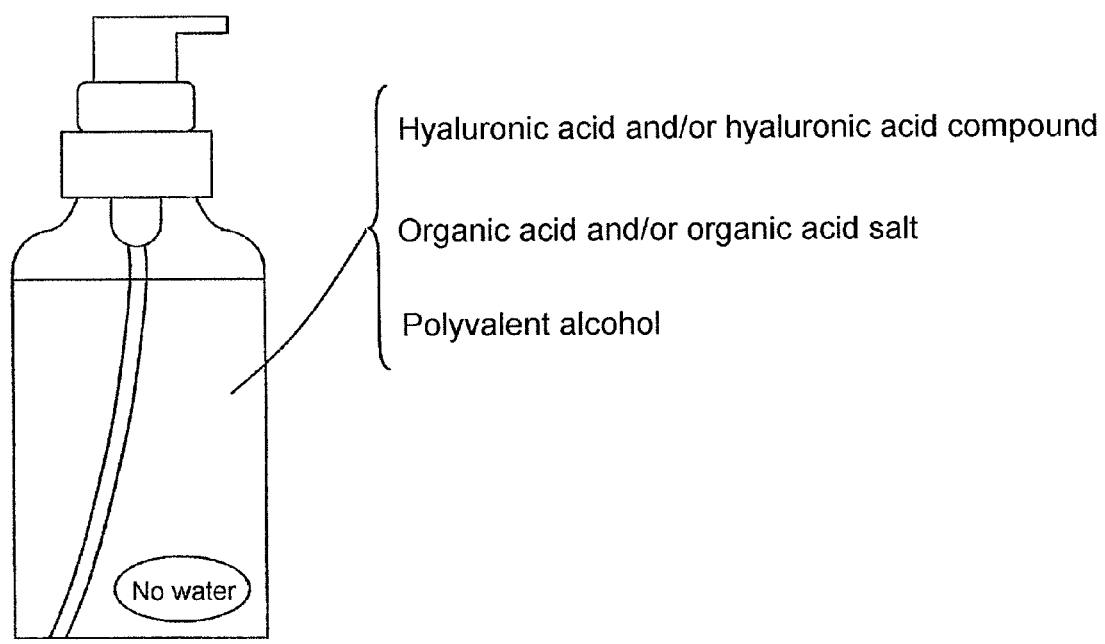
FIG. 1 is a view showing the configuration of the cosmetic solution according to the embodiment of the present invention.

As shown in FIG. 1, the cosmetic solution according to the embodiment of the present invention is obtained by dispersing hyaluronic acid and/or the hyaluronic acid compound in a polyvalent alcohol, and by dispersing an organic acid and/or an organic acid salt different from the hyaluronic acid and/or the hyaluronic acid compound in the polyvalent alcohol to allow the solution to be weakly acidic having a pH of $5 \leq pH < 7$ such that no water is contained.

As the hyaluronic acid compound, a hyaluronic acid salt can be given, for example. As the hyaluronic acid salt, salts of an inorganic acid such as hydrochloric acid, sulfuric acid, phosphoric acid and hydrobromic acid; salts of an organic acid such as acetic acid, lactic acid, maleic acid, fumaric acid, tartaric acid, citric acid, methanesulfonic acid, and p-toluenesulfonic acid; and sodium salts, potassium salts, ammonium salts, magnesium salts, calcium salts, zinc salts and cobalt salts or the like can be given. In addition, derivatives of hyaluronic acid can also be used. Specifically, acetylated hyaluronic acid, hyaluronic acid methyl ester, or one in which a protective group is introduced into a carboxyl group or a hydroxyl group of hyaluronic acid is introduced, or the like can be given.

In the invention, no specific restrictions are imposed on the molecular weight of the hyaluronic acid and/or the hyaluronic acid compound used. The hyaluronic acid and/or the hyaluronic acid compound is well absorbed by the skin, thus giving no sticky feeling to the skin, and exhibits effects of increasing the amount of water of stratum corneum. In addition, it has property of capable of keeping the moisture-retaining property constant without being affected by the moisture in the air.

As the hyaluronic acid and/or the hyaluronic acid compound, a widely used sodium hyaluronate is known, for example. Sodium hyaluronate is produced on the industrial basis by a method in which it is extracted from animal tissues or the like such as cockscomb of a chicken and the skin of an animal or by a fermentation method in which a microorganism is cultured. Sodium hyaluronate which is used in the invention may be produced either by the extraction method or by the fermentation method. In general, the molecular weight of sodium hyaluronate is diversified, ranging from a relatively small molecular weight to a large molecular weight of several hundred millions. In the invention, any of sodium hyaluronate having a small molecular weight to sodium hyaluronate having a large molecular weight can be used.

As the polyvalent alcohol, a divalent alcohol (for example, ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol, or the like), trivalent alcohol (for example, glycerin, trimethylolpropane, or the like), tetravalent alcohol (for example, pentaerythritol such as 1,2,6-hexane triol, or the like), pentavalent alcohol (for example, xylitol, or the like); hexavalent alcohol (for example, sorbitol, mannitol, or the like), polyvalent alcohol polymer (for example, diethylene glycol, dipropylene glycol, triethylene glycol, polypropylene glycol, tetraethylene glycol, diglycerine, polyethylene glycol, triglycerin, tetraglycerin, polyglycerin, or the like) can be used singly or in combination of two or more.

As the polyvalent alcohol, glycerin alone or a mixture of glycerin with other polyvalent alcohols can be used. The amount of glycerin is 50 wt % or more, preferably 80 wt % or more, and more preferably 90 wt % or more relative to the amount of the cosmetic solution.

Glycerin is a natural skin moisturizing component generated by the decomposition of a sebum in the skin. Glycerin is the oldest moisturizing agent, and gives moisture and a moist feeling to the skin. Therefore, in cooperation with the hyaluronic acid and/or the hyaluronic acid compound, glycerin synergistically improves the moisturizing power.

As an organic acid, citric acid, ascorbic acid, succinic acid, tartaric acid, lactic acid, tannic acid, malic acid, acetic acid, oxalic acid, etc. can be given, for example.

As an organic acid salt, a sodium salt, a potassium salt, an ammonium salt, a magnesium salt, a calcium salt or the like of the above-mentioned organic acid can be given.

These organic acids or organic acid salts can be used singly or in combination of two or more. By dispersing the organic acid and/or the organic acid salt in a polyvalent alcohol, the pH of the resulting solution is allowed to be weakly acidic, i.e. a pH of $5 \leq pH < 7$.

In the embodiment, citric acid is used. Citric acid is an organic compound contained in oranges or the like, and one of hydroxy acids, which is a colorless or white solid at normal temperature. Due to the dispersion of citric acid, a weakly acidic state can be attained. The reason for using citric acid is that it is an organism component which is used as a food additive and has a high degree of safety.

The cosmetic solution of the invention contains the hyaluronic acid and/or the hyaluronic acid compound in an amount of 0.01 to 2.0 wt % and contains a polyvalent alcohol in an amount of 97 wt % or more.

If the content is smaller than 0.01 wt %, the moisturizing effects are hardly exhibited. On the other hand, if the content exceeds 2.0 wt %, the dispersed hyaluronic acid and/or hyaluronic acid compound cannot be dissolved completely in a polyvalent alcohol and tend to be precipitated, whereby the quality may be deteriorated.

It is desired that the hyaluronic acid and/or hyaluronic acid compound be contained in an amount of 0.1 to 1.0 wt %. With this amount range, it is possible to disperse and dissolve the hyaluronic acid and/or hyaluronic acid compound completely.

The cosmetic solution of the invention contains citric acid in an amount of 0.0005 to 0.2 wt %. If the amount of the citric acid is less than 0.0005 wt %, the effects are not significant, and the pH thereof becomes closer to neutral. On the other hand, if the amount of citric acid exceeds 0.2 wt %, the acidity becomes too high.

The amount of citric acid is preferably 0.001 to 0.1 wt %, more preferably 0.005 to 0.07 wt %, and further preferably 0.01 to 0.04 wt %.

When the cosmetic solution containing citric acid in this amount range is dissolved in water, the resulting aqueous solution becomes ideal weakly acidic.

Next, an explanation will be made on the method for producing the cosmetic solution according to the embodiment of the present invention.

Figure 2:
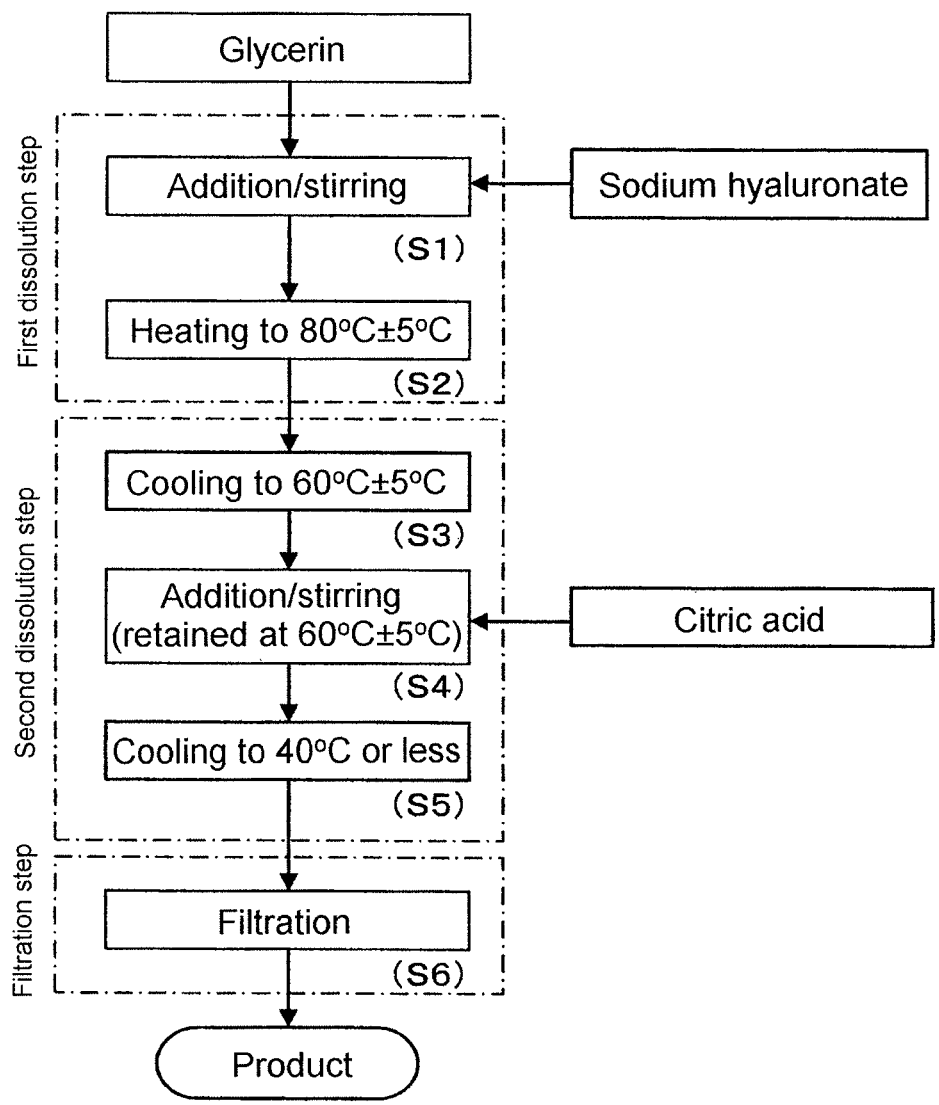
FIG. 2 is a flow chart showing the method for producing the cosmetic solution according to the embodiment of the invention.

As shown in FIG. 2, in the embodiment, sodium hyaluronate is used as the hyaluronic acid and/or hyaluronic acid compound. The polyvalent alcohol is composed of glycerin alone. As the organic acid and/or organic acid salt, citric acid as the organic acid is used. The method for producing the cosmetic solution according to the embodiment of the invention comprises a first dissolution step of adding to and dissolving in a solution of a polyvalent alcohol (glycerin) hyaluronic acid and/or a hyaluronic acid compound; and a second dissolution step of adding to and dissolving in the solution after this first dissolution step an organic acid (citric acid) and/or an organic acid salt to allow the mixture to be weakly acidic having a pH of $5 \leq pH < 7$; and a filtration step.

In this case, sodium hyaluronate and citric acid are independently a material which is hardly dissolved in glycerin. Therefore, if they are added simultaneously, in the case where dissolution does not proceed, it is impossible to confirm visually the dissolution state, i.e. to confirm which material is not dissolved. However, according to the method of the present invention, these materials are added in separately, i.e. the first dissolution step and the second dissolution step, it is possible to confirm the dissolution state, and as a result, dissolution can be attained without fail.

Citric acid serves to adjust pH. Citric acid affects the pH greatly even when used in a small amount, since the citric acid is added later in the second dissolution step, the amount thereof can be adjusted in accordance with the conditions in the first dissolution step such as the amount of the solution or the like. The adjustment of pH can be conducted without fail, and as a result, a high-quality cosmetic solution can be produced.

Specifically, in the first dissolution step, a solution of glycerin is heated to 30° C. to 70° C., desirably 60° C.±5° C. During or after this heating step, sodium hyaluronate is added and stirred (S1), and subsequently, this solution is heated to 80° C.±5° C., thereby to dissolve the sodium hyaluronate (S2).

If the temperature of the glycerin is lower than 30° C., stirring cannot be conducted easily due to the stickiness of the glycerin. If the temperature of the glycerin exceeds 70° C., due to the affection of vapor, sodium hyaluronate tends to adhere to the container (kettle). By adding sodium hyaluronate during or after heating the solution of glycerin to 60° C.±5° C., stirring can be conducted easily, whereby dissolution can be attained without fail. After the addition of sodium hyaluronate, the solution is heated to 80° C.±5° C. while stirring. By this, sodium hyaluronate can be dissolved in the glycerin with a higher degree of accuracy.

When homogeneous dissolution of the sodium hyaluronate is confirmed, the solution is cooled to 60° C.±5° C. in the second dissolution step (S3). Citric acid is added in this state and stirred (S4). When homogeneous dissolution of citric acid is confirmed, the solution is cooled to 40° C. or less (S5).

The reason for adding citric acid not to the solution heated to 80° C.±5° C., but to the solution cooled to 60° C.±5° C. is that, if the temperature is high, adjustment is difficult such as a change in pH or the like. Therefore, although it is desired that citric acid be added at a temperature at which the cosmetic solution is used, if the temperature is too low, the solution is hardly dissolved. By dissolving citric acid in a solution heated to 60° C.±5° C., citric acid can be easily dissolved and adequate pH adjustment can be conducted. Further, since the solution is cooled to 40° C. or less, stabilization can be promoted.

After the second dissolution step, in a filtration step, the solution is filtrated to remove sodium hyaluronate which is not dissolved in glycerin (S6). In this case, since sodium hyaluronate which is not dissolved in glycerin is removed by filtration, quality can be improved. In the meantime, if sodium hyaluronate is completely dissolved without being precipitated, a filtration step is not needed to be provided.

Then, the solution is put in a container to allow it to be a product. By doing this, due to the storage in the liquid state, the cosmetic solution contains no water and, unlike the conventional powder, due to its liquid state, water is hardly absorbed when it contacts the air, whereby proliferation of microorganisms such as bacterium and mold can be prevented, thereby significantly improving the storage storability.

Subsequently, an explanation is made on the cosmetic method according to the embodiment of the invention. The cosmetic method according to the embodiment is a basic skin care which is conducted by only <cosmetic solution application step> or in the order of <make up removing step>→<face-washing step>→<cosmetic solution application step>→<finishing step>. That is, at first, make up is removed by using a make-up remover. Subsequently, face washing is conducted, and the cosmetic solution is applied in order to moisturize the skin, and finally, an oil film is formed on the skin to keep the water content thereof, thereby to soften the skin. Needless to say, in the case of a bare skin which does not require make-up removal, the cosmetic method may only be conducted in the order of <cosmetic solution application step>→<cosmetic solution application step>→<finishing step>. Alternatively, it may be conducted in the order of <cosmetic solution application step>→<finishing step>. Or, it may be conducted in the order of <face-washing step>→<cosmetic solution application step>→<finishing step>. The order may be changed appropriately.

Each step may be explained in detail.

<Make-Up Removing Step>

This is a step for removing make up by using a cleansing agent. As the cleansing agent, an only oily material containing no synthetic surfactant is used.

As the oily material, vegetable oil, animal oil and waxes derived from a natural resource are used as they are after refining. Alternatively, they can be used as a derivative after the steps of hydrolysis, hydrogenation, high-pressure hydrogen reduction, esterification or the like. Examples of the oily material include avocado oil, linseed oil, argan oil, almond oil, perilla oil, olive oil, cocoa butter, carrot extract, karo philamlife ino philamlife oil, cucumber oil, candle nut oil, theobroma grunge furoru seed fat, kuranbeabishi nica seed oil, grape seed oil, sesame oil, wheat germ oil, oryza oil, rice bran oil, safflower oil, shea butter, soybean oil, tea oil, evening primrose oil, camellia oil, corn oil, rapeseed oil, persic oil, palm oil, hydrogenated palm oil, palm kernel oil; Coix oil, pistachio nut oil, castor oil, hydrogenated castor oil, sunflower oil, hazelnut oil, hydrolyzed hazelnut protein, hemp oil, borage oil, macadamia nut oil, mango butter, meadowfoam oil, cottonseed oil, tallow, coconut oil, yucha oil, peanut oil, rose hip oil, orange roughy oil, beef tallow, turtle oil, mink oil, egg yolk oil, jojoba oil, beeswax, lanolin, lanolin derivatives, hydrogenated lanolin, α-olefin oligomers, hydrogenated polydecene, squalane, vegetable squalane, mineral oil, petrolatum and mixtures thereof.

In this make-up removing step, since a cleansing agent containing no synthetic surfactant is used, it is impossible to wash make-up off. If the make up is alienated, the make-up is removed by gently putting by tissue paper or the like.

In general, oily make-up cannot be removed only by a facial cleanser. Therefore, a washable facial cleanser which is obtained by compounding an oily component that is easily blended with the make-up with a synthetic surfactant is commonly used. A synthetic surfactant serves to help mixing of materials which are not mixed with each other due to difference in surface tension, such as water and oil, and allows these materials to be merged with each other. It has been pointed out that such a synthetic surfactant, when applied to the skin, tends to induce an irritation reaction on the skin due to its relative capability of partially dissolving the sebum membrane of the skin surface, and that a synthetic surfactant is bonded to the stratum corneum protein of the surface skin, causing rough skin. In addition, if a synthetic surfactant is released to the environment, it affects adversely the ecology of water creatures.

Therefore, as in the embodiment of the present invention, by using a cleansing agent containing no synthetic surfactant, a state in which an irritation reaction is induced on the skin is prevented, whereby rough skin can be avoided.

<Face-Washing Step>

This is a step where face is washed by using a facial cleanser. As the facial cleanser, soap containing no synthetic surfactant is used. Soap is a general term of salts of a higher fatty acid, and is a natural surfactant. In this step, an oily component remaining on the skin after the make-up removing step is washed off by a natural surfactant of soap. As the method for producing soap, a saponification method and a neutralization method can be given. Soap can be produced by any method as long as it does not contain a synthetic surfactant.

In general, face-washing cream and face-washing foam is prepared by compounding fatty acid soap or other synthetic surfactants with a moisturizing agent, an oil component or the like. As mentioned above, it has been pointed out that a synthetic surfactant tends to induce an irritation reaction on the skin, causing rough skin. As in the embodiment of the present invention, by using soap containing no surfactant as the facial cleanser, a state in which an irritation reaction is induced on the skin is prevented, and rough skin can be prevented. As a result, effects obtained by the make-up removing step can be maintained more surely.

<Cosmetic Solution Application Step>

This is a step in which the cosmetic solution according to the embodiment of the invention is applied to the skin. When used, a necessary amount of the solution is discharged by means of a container. For example, the amount every time a user uses is discharged on the palm or the like, and the cosmetic solution is used as it is, or is used after mixing with fresh water. If it is used as it is, it feels heavy due to the viscosity thereof. Therefore, water is used in general. As water, tap water is sufficient. It is preferred that tap water from which chlorine that irritates the skin is removed by means of a water purifier or a water available in a PET bottle be used. When mixed with water, the water is used in an amount of 0.5 to 100 times, preferably 5 to 50 times, more preferably 10 to 20 times larger than the dead weight of the cosmetic solution. In this case, as compared with the conventional powder, due to its liquidity, it is needless to say that mixing is easy not only when it is used as it is but also after diluting with fresh water, resulting in a significantly easy handling.

In this case, In general, the surface of healthy skin is weakly acidic (pH 5.5 to 6.0). Immediately after washing with alkaline soap, the skin surface is more likely to be alkaline in the face-washing step. If the cosmetic solution of the present invention is used in this state, since the cosmetic solution of the present invention is weakly alkaline due to the presence of citric acid, it is possible to recover the skin to the weakly alkaline state immediately. As a result, the barrier function or the physiological function of the skin can be kept in the normal state, the healthy skin can be maintained.

In the state where the cosmetic solution of the present invention is applied to the skin, since no antiseptic is mixed, there is no irritation to the skin caused by an antiseptic. Therefore, the state of the skin becomes quite healthy. The hyaluronic acid cooperates with the polyvalent alcohol to exhibit moisturizing function, whereby moisture-retaining property is improved, and elasticity, moisture or firmness can be given to beautify the skin.

Further, in this case, a cleansing agent or soap containing no synthetic surfactant is used in the make-up removing step and the face-washing step, a state where an irritation reaction is induced on the skin is avoided, and rough skin is prevented, the effects of applying the cosmetic solution of the present invention can be exhibited more surely.

<Finishing Step>

This is a step where a finishing agent is applied to the skin. As the finishing agent, only an oily material which does not contain a synthetic surfactant is used. This finishing agent is used instead of a milky lotion or cream which is commonly used.

As the oily raw material, vegetable oil, animal oil and waxes derived from a natural resource are used as they are after refining. Alternatively, they can be used as a derivative after the steps of hydrolysis, hydrogenation, high-pressure hydrogen reduction, esterification or the like. Examples of the oily material include avocado oil, linseed oil, argan oil, almond oil, perilla oil, olive oil, cocoa butter, carrot extract, karo philamlife ino philamlife oil, cucumber oil, candle nut oil, theobroma grunge furoru seed fat, kuranbeabishi nica seed oil, grape seed oil, sesame oil, wheat germ oil, oryza oil, rice bran oil, safflower oil, shea butter, soybean oil, tea oil, evening primrose oil, camellia oil, corn oil, rapeseed oil, persic oil, palm oil, hydrogenated palm oil, palm kernel oil, coix oil, pistachio nut oil, castor oil, hydrogenated castor oil, sunflower oil, hazelnut oil, hydrolyzed hazelnut protein, hemp oil, borage oil, macadamia nut oil, mango butter, meadowfoam oil, cottonseed oil, tallow, palm oil, coconut oil, yucha oil, peanut oil, rose hip oil, orange roughy oil, beef tallow, turtle oil, mink oil, egg yolk oil, jojoba oil, beeswax, lanolin, lanolin derivatives, hydrogenated lanolin, α-olefin oligomers, hydrogenated polydecene, squalane, vegetable squalane, mineral oil, petrolatum and mixtures thereof.

In this finishing step, by using an oily material containing no synthetic surfactant after application of a cosmetic solution, evaporation of water can be prevented by the blockage effect of the skin, whereby moisturizing of the skin is promoted. In general, a milky lotion and cream are obtained by emulsifying water, a moisturizing component and an oily component by a synthetic surfactant. By applying it to the skin on which the cosmetic solution has been applied, evaporation of watercan be prevented by the blockage effect of the skin, whereby moisturizing of the skin is promoted. As mentioned above, it has been pointed out that a synthetic surfactant tends to induce an irritation reaction on the skin, causing rough skin. However, as in the case of the present invention, by using a finishing agent containing no synthetic surfactant, occurrence of an irritation reaction on the skin can be prevented, whereby rough skin is avoided. As a result, the effects brought by the make-up removing step, the effects brought by the face-washing step and the effects brought by the cosmetic solution applied in the cosmetic solution application step can be exhibited further surely.

As mentioned above, in the case of a basic skin care in which <make-up removing step>→<face-washing step>→<cosmetic solution application step>→<finishing step> are conducted in this order, a series of process is conducted without using a synthetic surfactant and a preservative. As a result, the skin barrier is protected to keep the beautiful, healthy skin.

EXAMPLES

Then, a cosmetic solution according to the Examples is shown.

In the cosmetic solution in the Examples, sodium hyaluronate (also referred to as the "Na hyaluronate") ("hyaluronic acid FCH60" manufactured by Kibun Food Chemifa Co., Ltd.) was used.

As the citric acid, "citric anhydride" manufactured by Showa Kako Corp. was used.

As the polyvalent alcohol, "thick glycerin for cosmetic purpose" manufactured by Kao Corporation", 1,3-butylene glycol (often abbreviated as "BG") ("1,3-butylene glycol" manufactured by Daicel Corporation) and propylene glycol (often abbreviated as "PG") ("propylene glycol" manufactured by Azuma Co., Ltd.) were used singly or in combination.

Then, as shown in Table 1 below, the component ratio of each material is changed appropriately, whereby the products according to Examples 1 to 7 were produced in accordance with the above-mentioned production method (excluding the filtration method). In Example 1, the resulting solution had a pH of 5.24 (22.0° C.) and a viscosity of 17050 cps (20° C., a B type viscometer, No. 4 rotor, 12 rpm, 60 s).

For each Example and Comparative Example 1 (only glycerin), dissolution stability of each component (a state at which the components are sufficiently dissolved without being precipitated) was visually confirmed. The results are shown in Table 1. From the results of Example 3, the content of sodium hyaluronate was 2.0 wt % or less, which was a favorable result.

If the content of sodium hyaluronate exceeded 1.0 wt %, although stability was good, handling became difficult due to a high viscosity. Accordingly, it was understood that the content of sodium hyaluronate was in the range of 1.0 wt % or less.

TABLE 1

| Component | Examples | | | | | | | Comparative Examples |
|---|---|---|---|---|---|---|---|---|
| | 1 | 2 | 3 | 4 Glycerin:BG | 5 Glycerin:BG | 6 | 7 | 1 |
| Hyaluronic acid Na (60) | 0.5 | 1.0 | 2.0 | 0.5 | 0.5 | 0.5 | 0.5 | |
| Citric acid | 0.030 | 0.030 | 0.030 | 0.030 | 0.030 | 0.030 | 0.030 | |
| Glycerin | 99.470 | 98.970 | 97.970 | 49.735 | 9.947 | — | — | 100 |
| 1,3 butylene glycol (BG) | — | — | — | 49.735 | 89.523 | 99.470 | — | |
| Propylene glycol | — | — | — | — | — | — | 99.470 | |
| Stability | ◎ | ◎ | Δ (However, very viscous) | ◎ | ◎ | ◎ | ◎ | ◎ |

As for Examples 1 to 7 and Comparative Example 1, moisturizing power was evaluated. For the evaluation of moisturizing power, an oil water content measuring apparatus (WSK-P500U manufactured by Wave Cyber) was used. This measuring apparatus indicates the water content of the part of the skin to be measured by a relative value of 0 to 99. The part to be measured was the forearm flexor side. To the parts of the skin which have almost the same moisture content before application of a cosmetic solution, the cosmetic solution of Examples and Comparative Examples, which had been diluted twice by water, was applied and the moisture content was evaluated with the passage of time.

From the results, it was found that glycerin exhibited the highest moisturizing power as compared with propylene glycol and 1,3-butylene glycol. Further, it was found that when glycerin was used as a mixture with other polyvalent alcohols, it was preferred that glycerin be contained in an amount of 50 wt % or more relative to the total amount of polyvalent alcohols in order to exhibit an excellent moisturizing power.

In addition, a microbial test was conducted for Example 1, and Comparative Examples 2 and 3. As Comparative Example 2, purified water was prepared. As Comparative Example 3, a cosmetic solution obtained by mixing purified water, 0.05 wt % of sodium hyaluronate ("hyaluronic acid FCH60" produced by Kibun Food Chemical Co., Ltd), 5.00 wt % of glycerin ("concentrated glycerin for cosmetics" produced by Kao Chemicals) and 0.10 wt % of methylparaben ("Meckins M" produced by Ueno fine chemicals industry Co., Ltd.) as a preservative was prepared. After making each specimen of Example 1, Comparative Examples 2 and 3, the specimens were put in a beaker. The beaker containing the specimens was allowed to stand uncovered for 16 hours (left open) and exposed to air. After that, each specimen was transferred to a glass bottle with a lid which had been washed and sterilized. The bottle was put in a constant-temperature bath at 40° C., and cultivated. The specimens were taken out at 1 day, 4 days and 7 days, and the generation status of microorganism in the specimens was checked. The check of the generation status of microorganism was conducted by the following procedure. 0.2 ml of the specimen was taken out from the glass bottle. The specimen obtained was applied on a trypto-soy agar provided in a petri dish with a lid. The petri dish was put, with being covered, in a similar constant-temperature bath as mentioned above, and the generation status of microorganism was checked over 48 hours. The results are shown in Table 2 below. For the purified water as Comparative Example 2, since the generation of microorganism colony was found at the early stage, the test was interrupted after a lapse of 8 hours.

From the results, no generation of microorganism was observed in Example 1 in spite of the preservative-free state. The result was equivalent to that in Comparative Example 2 in which a preservative was used. Therefore, it was found that the cosmetic solution in Example 1 was excellent.

TABLE 2

| | Microbial test | | |
|---|---|---|---|
| | One-day cultivation | Four-day cultivation | Seven-day cultivation |
| Com. Ex. 2 | X (One) | X (500 or more) | X (500 or more) |
| Com. Ex. 3 | Zero | Zero | Zero |
| Example 1 | Zero | Zero | Zero |

Examples of a make-up method are shown below.
<Cleansing Step>
As the cleansing according to the Example, "olive squalane" 100% (produced by higher alcohols Industries, Ltd.) which is obtained by expressing squalane from the residue obtained by pressing olive oil of olive fruit, distilling, hydrogenating and purifying them was used. Olive squalane is chemically stable, has less oily feel and is very comfortable to touch. It gives very small skin irritation, has an excellent emollient effect, and hence, it is optimum oil to be used as cleansing oil.
<Face-Washing Step>
As the washing agent according to Example, a soap containing 80% of palm oil, 20% palm kernel oil and 5 to 10% of squalane (saponification rate: 85 to 95%, saponification by cold process) was used. A soap produced by the saponification cold process has a mild detergency since unreacted fats and glycerin remain.
<Cosmetic Solution Step>
As the cosmetic solution according to the Examples, one according to Example 1 was used.

Specifically, as sodium hyaluronate (also referred to as "hyaluronic acid Na"), "hyaluronic acid FCH60" (produced by Kibun Food Chemical Co., Ltd.) was used. As the citric acid, "citric anhydride" (produced by Showa Chemical Co., Ltd.) was used. As the polyvalent alcohol, glycerin ("concentrated glycerin for cosmetics" produced by Kao Chemicals) was used. The component ratio is as shown in Table 1. In Example 1, the pH was 5.24 (22.0° C.), the viscosity was 17050 cps (measured at 20° C. using a B-type viscometer and No. 4 rotor, at 12 rpm, at 60 s).
<Finishing Step>
As the finish agent according to Example, one obtained by hydrogenating squalane obtained from the liver oil of sharks that live in the deep sea was used. Squalane is chemically stable, and representative high-quality oil. It gives very small skin irritation, and has an excellent emollient effect. Further, one obtained by dissolving fullerene in squalane exhibits an antioxidant effect in addition to a moisturizing effect, whereby a slow-aging and beautiful skin can be maintained.

Then, the cosmetic solution according to Example 1 above was tested by panelers for usability. As the paneler, 50 adult women, including those who have got a lush when commercial basic skin-care products were used, were chosen. The thus chosen panelers used the cleansing agent according to Example 1, cosmetic solution according to Example, washing agent according to Example and finishing agent according to Example for a period of from 1 month to 1 year. They performed basic skin care in accordance with the <cleansing step>→<face washing step>→<cosmetic solution step>→<finish step>, and evaluated them. For the cosmetic solution, the panelers replaced their traditional solutions by the solution obtained by diluting the cosmetic solution of Example 1 with water to be 20 times in weight of the original, and evaluated them.

1. Regarding the moisturizing power
100%: Of 50 women, 50 experienced high moisturizing power as compared with the basic skin-care products that have been used up to now
0%: Of 50 women, nobody did not understand the difference or noted any difference between the basic skin-care products that have been used up to now
0%: Of 50 women, nobody experienced lower moisturizing power as compared with the basic skin-care products that have been used up to now 2. Regarding gentleness to the skin
Did you feel any unpleasant feel to the skin such as itching or tingling?
100%: Of 50 women, 50 answered NO
0%: Of 50 women, nobody answered YES 3. Do you want to continue to use?
98%: Of 50 women, 49 want to use very much
2%: Of 50 woman, only one wants to use if need arises
0%: Of 50 women, nobody answered neither YES or NO
0%: Of 50 women, nobody does not want to use From these results, it could be understood that, by conducting a series of skin care by using a cleansing agent, a cosmetic solution and a finishing agent which each does not contain a synthetic surfactant and a preservative, skin barrier can be protected, whereby a beautiful, healthy skin can be maintained without experiencing irritation to the skin. Further, it could be understood that the cosmetic solution according to Example 1 was significantly excellent.

In the embodiment of the invention, only hyaluronic acid and/or a hyaluronic acid compound, an organic acid and/or an organic acid salt were added to a polyvalent alcohol. The invention is not limited to this embodiment, and it is possible to mix with a polyvalent alcohol, other than hyaluronic acid and/or a hyaluronic acid compound, and an organic acid and/or an organic acid salt, other components except for a preservative and a synthetic surfactant that are commonly used in the field of skin science on the condition that they contain no water.

INDUSTRIAL APPLICABILITY

As for the cosmetic solutions which are used by 90% or more of adult women everyday, they are formed mainly of water. Taking into consideration that a large amount of such cosmetic solutions are distributed in the world, the cosmetic solution of the present invention is provided to consumers in the state that contains no water, bringing out various advantages relating to containers, storage spaces and transportation costs. Further, even if hyaluronic acid and/or a hyaluronic acid compound, which are expensive to be used in a cosmetic solution, are not used in a large amount, a high moisturizing power can be obtained by combined use of a polyvalent alcohol, thereby giving consumers great advantages.

Further, since the cosmetic solution does not contain a preservative and a synthetic surfactant, it gives no irritation to the skin. As a result, the cosmetic solution is significantly effective since the number of persons who suffer occurrence of rash is deceased, thereby to lead a reduction in medical expenses or other merits.

The invention claimed is:

1. A method for producing a cosmetic solution, comprising:
    a first dissolution step of adding to and dissolving in a solution of a polyvalent alcohol hyaluronic acid and/or sodium hyaluronate; and
    a second dissolution step of adding and dissolving an organic acid and/or an organic acid salt different from the hyaluronic acid and/or the sodium hyaluronate to allow the solution to be weakly acidic having a pH of 5≤pH<7,
    wherein the cosmetic solution contains 0.01 to 2.0 wt % of the hyaluronic acid and/or the sodium hyaluronate, and 97 wt % or more of the polyvalent alcohol, without water.

2. The method for producing the cosmetic solution according to claim 1, wherein, in the first dissolution step, the hyaluronic acid and/or the sodium hyaluronate is added to a solution of the polyvalent alcohol at 30° C. to 70° C., followed by stirring, and the solution is then heated to 80° C.±5° C.

3. The method for producing the cosmetic solution according to claim 1, wherein, in the second dissolution step, the solution is allowed to be 60° C.±5° C., and the organic acid and/or the organic acid salt is added at this temperature, followed by stirring, and the solution is then cooled to 40° C. or less.

4. The method for producing the cosmetic solution according to claim 1, further comprising a filtration step of filtering the solution to remove the hyaluronic acid and/or the sodium hyaluronate which is not dissolved in the polyvalent alcohol after the second dissolution step.

5. A cosmetic method, comprising;
    a cosmetic solution application step of applying the cosmetic solution prepared by the method according to claim 1 to a face of a predetermined subject,
    wherein, in the cosmetic solution application step, the cosmetic solution is applied as it is or is applied after being mixed with water in an amount of 0.5 to 100 times larger than a dead weight of the cosmetic solution.

6. The cosmetic method according to claim 5, further comprising a face-washing step of washing the face of the predetermined subject by using a facial cleanser before the cosmetic solution application step,
    wherein the facial cleanser comprises soap containing no synthetic surfactant.

7. The cosmetic method according to claim 6, further comprising a make-up removing step of removing make-up by using a cleansing agent before the face-washing step,
    wherein the cleansing agent comprises only oily material containing no synthetic surfactant.

8. The cosmetic method according to claim 5, further comprising a finishing step of applying a finishing agent to the skin after the cosmetic solution application step,
    wherein the finishing agent comprises only oily material containing no synthetic surfactant.

9. The method for producing the cosmetic solution according to claim 1, wherein the cosmetic solution contains 0.1 to 1.0 wt % of the hyaluronic acid and/or the sodium hyaluronate.

10. The method for producing the cosmetic solution according to claim 1, wherein the organic acid and/or the organic acid salt is citric acid, and
    an amount of the citric acid is 0.0005 to 0.2 wt %.

11. The method for producing the cosmetic solution according to claim 1, wherein polyvalent alcohol comprises glycerin or a mixture of glycerin and other polyvalent alcohols.

* * * * *